(12) United States Patent
Mohl

(10) Patent No.: US 11,754,077 B1
(45) Date of Patent: *Sep. 12, 2023

(54) DEVICE TO ASSIST THE PERFORMANCE OF A HEART

(71) Applicant: Miracor Medical SA, Awans (BE)

(72) Inventor: Werner Mohl, Altenmarkt-Thenneberg (AT)

(73) Assignee: Miracor Medical SA, Awans (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/308,958

(22) Filed: Apr. 28, 2023

Related U.S. Application Data

(60) Continuation of application No. 18/087,083, filed on Dec. 22, 2022, now Pat. No. 11,674,517, which is a
(Continued)

(30) Foreign Application Priority Data

Feb. 27, 2007 (AT) .................................. A 306/2007

(51) Int. Cl.
*A61M 60/148* (2021.01)
*F04D 13/02* (2006.01)
(Continued)

(52) U.S. Cl.
CPC ........... *F04D 13/027* (2013.01); *A61M 60/13* (2021.01); *A61M 60/148* (2021.01); *A61M 60/17* (2021.01); *A61M 60/237* (2021.01); *A61M 60/405* (2021.01); *A61M 60/419* (2021.01); *A61M 60/422* (2021.01); *A61M 60/523* (2021.01); *A61M 60/861* (2021.01); *A61M 60/414* (2021.01); *A61M 60/833* (2021.01)

(58) Field of Classification Search
CPC .. A61M 60/40; A61M 60/405; A61M 60/148; A61M 60/135; A61M 60/422; A61M 60/857; A61M 60/205; A61M 60/833; A61M 60/414; A61M 1/101; A61M 1/1015; A61M 1/1008; A61M 1/1031; A61M 1/1032; A61M 1/1036; A61M 1/1029; A61M 1/122; A61M 1/125; F04D 13/027
See application file for complete search history.

(56) References Cited

U.S. PATENT DOCUMENTS

| 4,135,253 A | 1/1979 | Reich et al. |
| 4,674,518 A | 6/1987 | Salo |

(Continued)

FOREIGN PATENT DOCUMENTS

| DE | 3616857 | 12/1987 |
| EP | 0075606 | 4/1983 |

(Continued)

OTHER PUBLICATIONS

Authorized Officer Malte Kaden, International Search Report for Application No. PCT/IB2008/000421, dated Nov. 7, 2008, 3 pages.
(Continued)

*Primary Examiner* — Tammie K Marlen
(74) *Attorney, Agent, or Firm* — Fish & Richardson P.C.

(57) ABSTRACT

A device to assist the performance of a heart with at least one pump that is formed as a rotary pump and driven via a magneto coupling.

30 Claims, 3 Drawing Sheets

Related U.S. Application Data continuation of application No. 17/446,046, filed on Aug. 26, 2021, now Pat. No. 11,572,879, which is a continuation of application No. 16/282,948, filed on Feb. 22, 2019, now Pat. No. 11,123,540, which is a continuation of application No. 14/454,965, filed on Aug. 8, 2014, now Pat. No. 10,251,984, which is a continuation of application No. 13/555,318, filed on Jul. 23, 2012, now Pat. No. 8,801,590, which is a division of application No. 12/449,632, filed as application No. PCT/IB2008/000421 on Feb. 27, 2008, now Pat. No. 8,255,050.

(51) Int. Cl.
| | |
|---|---|
| *A61M 60/405* | (2021.01) |
| *A61M 60/422* | (2021.01) |
| *A61M 60/17* | (2021.01) |
| *A61M 60/13* | (2021.01) |
| *A61M 60/237* | (2021.01) |
| *A61M 60/523* | (2021.01) |
| *A61M 60/861* | (2021.01) |
| *A61M 60/419* | (2021.01) |
| *A61M 60/414* | (2021.01) |
| *A61M 60/833* | (2021.01) |

(56) References Cited

U.S. PATENT DOCUMENTS

| | | | |
|---|---|---|---|
| 4,895,557 | A | 1/1990 | Moise et al. |
| 5,308,319 | A | 5/1994 | Ide et al. |
| 5,449,342 | A | 9/1995 | Hirose et al. |
| 5,470,208 | A | 11/1995 | Kletschka |
| 5,503,615 | A | 4/1996 | Goldstein |
| 5,601,418 | A | 2/1997 | Ohara et al. |
| 5,921,913 | A | 7/1999 | Siess |
| 5,928,131 | A | 7/1999 | Prem |
| 5,964,694 | A | 10/1999 | Siess et al. |
| 6,007,478 | A | 12/1999 | Siess et al. |
| 6,083,260 | A | 7/2000 | Aboul-Hosn |
| 6,155,969 | A | 12/2000 | Schima et al. |
| 6,176,848 | B1 | 1/2001 | Rau et al. |
| 6,506,146 | B1 | 1/2003 | Mohl |
| 6,508,787 | B2 | 1/2003 | Erbel et al. |
| 6,540,658 | B1 | 4/2003 | Faschiano |
| 6,623,475 | B1 | 9/2003 | Siess |
| 7,699,586 | B2 | 4/2010 | LaRose et al. |
| 8,255,050 | B2 | 8/2012 | Mohl |
| 8,512,012 | B2 | 8/2013 | Akdis et al. |
| 9,616,157 | B2 | 4/2017 | Akdis |
| 2001/0039369 | A1* | 11/2001 | Terentiev ............ A61M 60/876 600/16 |
| 2004/0236420 | A1 | 11/2004 | Yamane et al. |
| 2006/0089521 | A1 | 4/2006 | Chang |
| 2008/0214888 | A1 | 9/2008 | Ben Shalom |
| 2011/0238172 | A1* | 9/2011 | Akdis .................. A61M 60/117 623/3.11 |

FOREIGN PATENT DOCUMENTS

| | | |
|---|---|---|
| EP | 0503839 | 9/1992 |
| EP | 1011753 | 6/2000 |
| EP | 1034808 | 9/2000 |
| EP | 1727987 | 12/2006 |
| FR | 1187249 | 8/1959 |
| GB | 2347085 | 8/2000 |
| JP | 2005348996 | 12/2005 |
| WO | WO 1993/20860 | 10/1993 |
| WO | WO 1997/37698 | 10/1997 |
| WO | WO 1999/15213 | 4/1999 |
| WO | WO 2000/44417 | 8/2000 |
| WO | WO 2001/70300 | 9/2001 |

OTHER PUBLICATIONS

Merkel et al., "Magnetic Bearing in INCOR Axial Blood Pump Acts as Multifunctional Sensor," Ninth International Symposium on Magnetic Bearings, 2004, 3 pages.

Mohl et al., "Intermittent Pressure Elevation of the Coronary Venous System as a Method to Protect Ischemic Myocardium," Interactive Cardio Vascular and Thoracic Surgery, vol. 4, 2005, pp. 66-69.

Ramsden et al., "A Rotary Blood Pump," University of Technology, Sydney, Mar. 2007, 4 pages.

Syeda et al., "The Salvage Potential of Coronary Sinus Interventions: Meta-Analysis and Pathophysiologic Consequences," The Journal of Thoracic and Cardiovascular Surgery, vol. 127, No. 6 (Jun. 2004), pp. 1703-1712.

\* cited by examiner

DEVICE TO ASSIST THE PERFORMANCE OF A HEART

CROSS-REFERENCE TO RELATED APPLICATIONS

This application is a continuation of and claims priority to U.S. application Ser. No. 18/087,083 filed on Dec. 22, 2022, which is a continuation of and claims priority to U.S. application Ser. No. 17/446,046 filed on Aug. 26, 2021 (now U.S. Pat. No. 11,572,879), which is a continuation of U.S. application Ser. No. 16/282,948 filed on Feb. 22, 2019 (now U.S. Pat. No. 11,123,540), which is a continuation of U.S. application Ser. No. 14/454,965 filed on Aug. 8, 2014 (now U.S. Pat. No. 10,251,984), which is a continuation of U.S. application Ser. No. 13/555,318 filed on Jul. 23, 2012 (now U.S. Pat. No. 8,801,590), which is a divisional of U.S. application Ser. No. 12/449,632 filed on Aug. 18, 2009 (now U.S. Pat. No. 8,255,050), which is the U.S. national phase of International Application PCT/IB2008/000421 filed on Feb. 27, 2008, which designated the U.S. and claims benefit of AT A 306/2007 filed Feb. 27, 2007, the entire contents of these prior applications are hereby incorporated by reference.

BACKGROUND

After a heart failure, for example a cardiac infarction or other reasons for the decrease in the performance of a heart, it is of essential importance for intensive care medicine to normalise and stabilise the cardiac function again as rapidly as possible. When for example the volume output of the heart is distinctly reduced as a result of a failure, it is particularly important to reliably and rapidly re-establish a corresponding peripheral blood flow in order to prevent secondary damage. The use of heart-lung machines basically allows the essential vital functions to be maintained. A specific adaptation to the respective actual requirements generally does not take place with such devices, however. Rather, conventional heart-lung machines are devices which, using external pumps, maintain a forced circulation of blood without systematically entering into the respective requirements of the heart which has been weakened or subjected to a failure. In surgical interventions, particularly in the vein area, it has already been proposed to carry out retroinfusion, controlled by venous pressure, from or in veins of the body with the suction" of fluid and return of the fluid via a pump. Conventional catheters are used here, the lumina of which allow a suction of fluid and via the lumina of which the return is made possible at a suitable site. Known devices, particularly for the retroinfusion of blood in coronary veins in the area of myocardial protection during a brief coronary artery closure within a cardiological intervention, are generally devised so that a balloon dilatation of an arteriosclerotically constricted coronary artery is carried out. In these cases, a compensation which is adapted to the intervention briefly taking place respectively can be carried out by the return of blood which has been drawn off in veins. For a continuous restitution of the full function of a heart, however, the criteria are not taken into account which would be relevant for the full function of the heart, and an intensive provision over a particular period of time is therefore not provided with such devices. At the same time, the provision of the other organs must also be maintained.

In the device known from AT 407 960 B for assisting the performance of a heart, fluid is removed from blood vessels via an external pump and is returned into blood vessels via a return catheter, in which the returned quantity of fluid is regulated as a function of measurement values, with a heart ventricle catheter being provided to obtain these measurement values. The known device comprised a heart ventricle catheter which is equipped in the cardiac chamber with sensors to measure the volume of fluid per unit of time, in which these sensors, in the introduced state of the heart ventricle catheter, lie in the cardiac chamber and these sensors are connected with an evaluation circuit in which the ratio of the diastolic volume to the systolic volume is evaluated per heartbeat or per unit of time in particular the discharge rate and/or the deviation of the volume conveyed per unit of time by the heart from a defined rated value is evaluated, for example the rated value, calculated from physically specific data for the cardiac output. The signal which is generated in this way is passed to the pump, via which fluid is withdrawn from the cardiac chamber and is recirculated as a function of the generated signal.

SUMMARY

A fluid flow which is improved by the pump is to be developed in a way in which the mechanical stress of highly sensitive fluids, such as blood for example, can be kept as low as possible and nevertheless the corresponding improvement to circulation can be ensured at desired locations. A completely impervious separation of the rotor from the drive wheel is achieved by a magneto coupling which is provided according to the invention, which eliminates axial passages between the drive wheel and the rotor lying distally on the outside.

The rotor itself can follow design principles such as described for example in WO 01/70300 A1. The rotary pump shown and described there for conveying blood and other highly sensitive fluids is formed as an external electromagnetically driven pump which is not directly suitable for incorporation into a catheter. However, for the desired conveying capacity with the axial pump according to the invention, provision is also made according to the invention that the rotor has guide surfaces to produce centrifugal flow components.

The driving fluid can be used within the scope of the invention in order to be able to operate a balloon for retroperfusion. The embodiment is preferably devised hereby so that the lumina for the driving fluid are guided through an expandable balloon surrounding the catheter in a sealing manner, and that the lumina have separately controllable closure members via which driving fluid can arrive in the balloon or out of the balloon into the respective lumina, in which preferably the closure members are formed as magneto valves. On inflation of the balloon, additional driving medium is required which can be discharged again on collapsing of the balloon. This is possible extracorporally on the drive side by means of a reservoir.

The embodiment to assist the performance of a heart according to the invention, in which fluid is conveyed in blood vessels with the use of a pump and the conveyed quantity is able to be regulated as a function of measurement values of a heart ventricle catheter, from which the cardiac output is determined, proceeds from a development according to AT 407 960 B and is characterised substantially in that the pump is formed as an intravasal rotary pump at the periphery or at the distal end of the catheter, the rotor of which, lying on the outside, is connected via a magneto coupling with the drive which is arranged inside the catheter.

BRIEF DESCRIPTION OF DRAWINGS

The invention is explained in further detail below by use of an exemplary embodiment which is illustrated diagrammatically in the drawings, in which.

DETAILED DESCRIPTION

Figure 1:
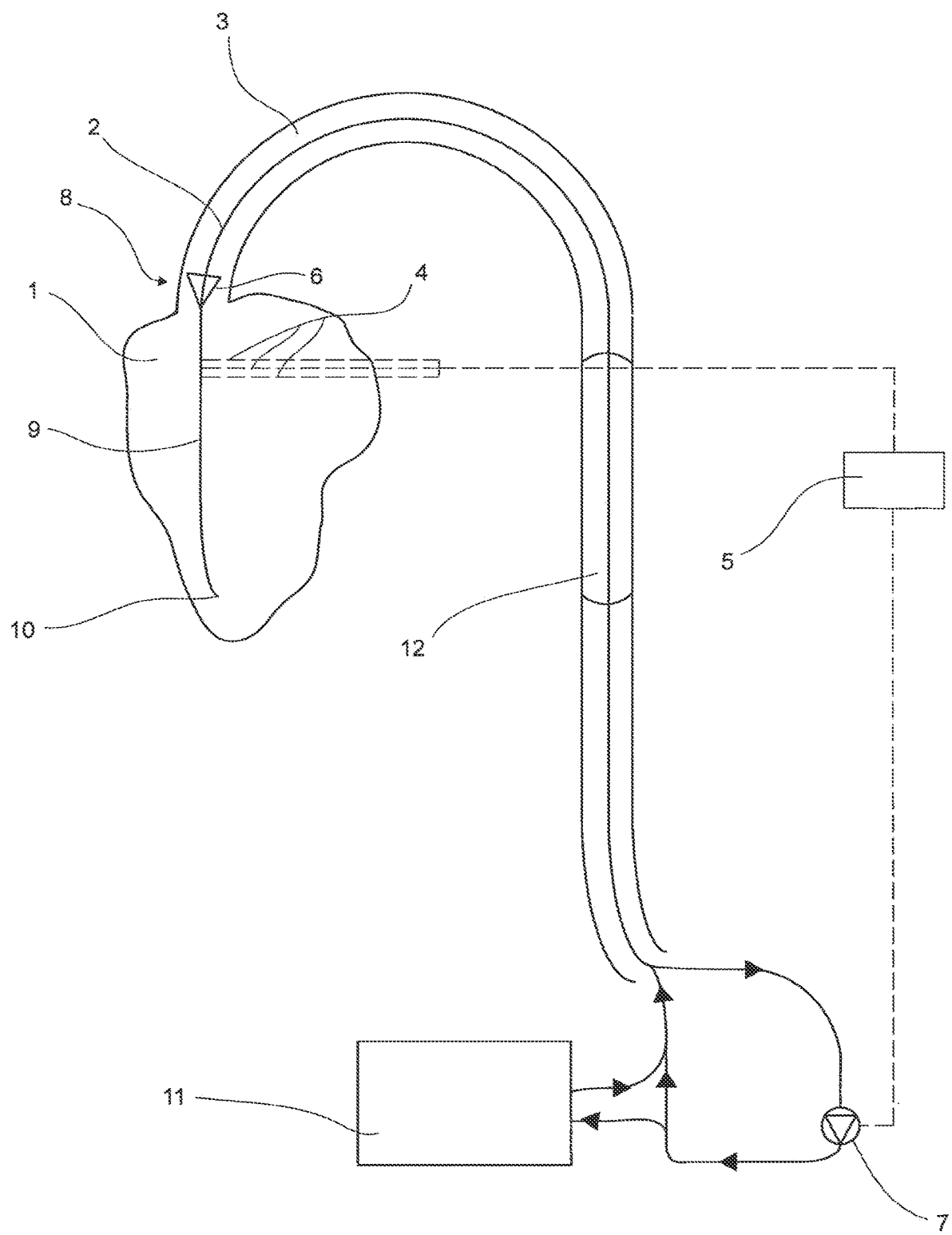
FIG. 1 shows a diagrammatic illustration of the arrangement of the pump and of the drive.

In FIG. 1, a heart is designated by 1, into which a heart ventricle catheter 2 is introduced. The catheter is introduced here for example via the femoral artery and the aortic arch 3 into the heart chamber and carries a series of sensors 4 via which the volume can be determined. The measurement signals are passed to a control arrangement 5. The heart ventricle catheter is formed with several lumina, as additionally illustrated below in further figures of the drawings, with fluid being supplied via such lumina to drive a rotor, arranged at the distal end, which forms the pump to assist the blood circulation and is designated by 6 in FIG. 1. The positioning of this rotor is indicated in FIG. 1 by the arrow 8. The driving medium for the rotor or the pump is guided in a circular flow by means of a fluid pump 7 which can be regulated in a synchronised manner as a function of the control signals generated in the control arrangement 5. The distal region in which the pump is arranged is designated diagrammatically by 8, the catheter 2 having at its distal end a tube 9 leading to the suction end 10. A reservoir for driving fluid is designated by 11, which provides additional driving medium for filling the balloon 12 serving for an occlusion of the artery, and which receives again the volume of driving medium occurring on deflation of the balloon.

The volumetric measurement in the cardiac chamber allows differences to be reliably detected between the diastolic and systolic volume and allows corresponding correction signals to be made available for the output of the synchronised fluid pump 7. Furthermore, in the control circuit 5, corresponding fixed values can be provided, such as for example a defined cardiac output, which is referred to on deviation of the measured cardiac output to control the pump.

A retroperfusion can take place via a conventional balloon catheter which is occluded in a correspondingly synchronized manner, so that the directed return is in fact guaranteed during the diastole. Hereby the corresponding measurement values for the heart rate or for the correct moment of the diastole can be obtained from ECG data.

Figure 2:
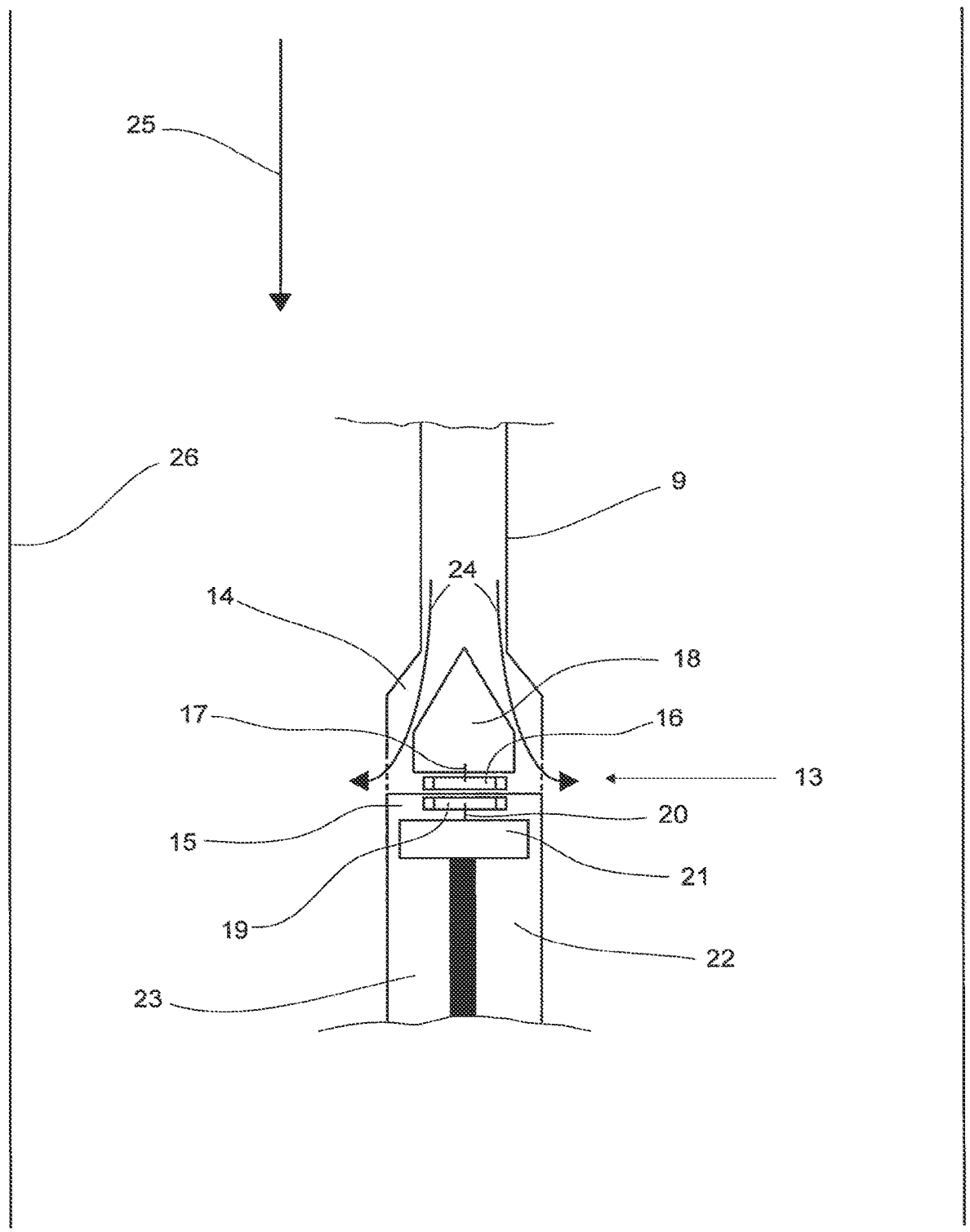
FIG. 2 shows a diagrammatic illustration of the distal end of a catheter which is used according to the invention.

In FIG. 2, the distal end of a modified catheter 2 is now illustrated. The end side 13 of this catheter has two pocket-shaped chambers 14 and 15, in which bar magnets are respectively arranged. The bar magnet 16 is connected here at the distal end outwards via a shaft 17 with a rotor 18, whereas the bar magnet 19 lying on the inside is connected via a shaft 20 with a drive wheel 21. The drive wheel 21 is formed here as a paddle wheel and is acted upon with fluid via a lumen 22, this fluid flowing off again via the lumen 23 of the catheter. The rotation of the paddle wheel 21 is regulated here accordingly by corresponding control of the fluid pressure in the lumen 22 serving for the supply of fluid, in which the magnet 19, which is connected so as to be locked against relative rotation with the paddle wheel 21, is set into corresponding rotation. At the outer side, which is completely sealed with respect to the lumina 22 and 23, the magnet 16 is subsequently entrained accordingly and drives the rotor 18 via the shaft 17, whereby a flow is formed in the region of the tube 9, as is indicated by the arrows 24, and which assists the natural blood flow in the vessel 26, illustrated by the arrow 25.

Figure 3:
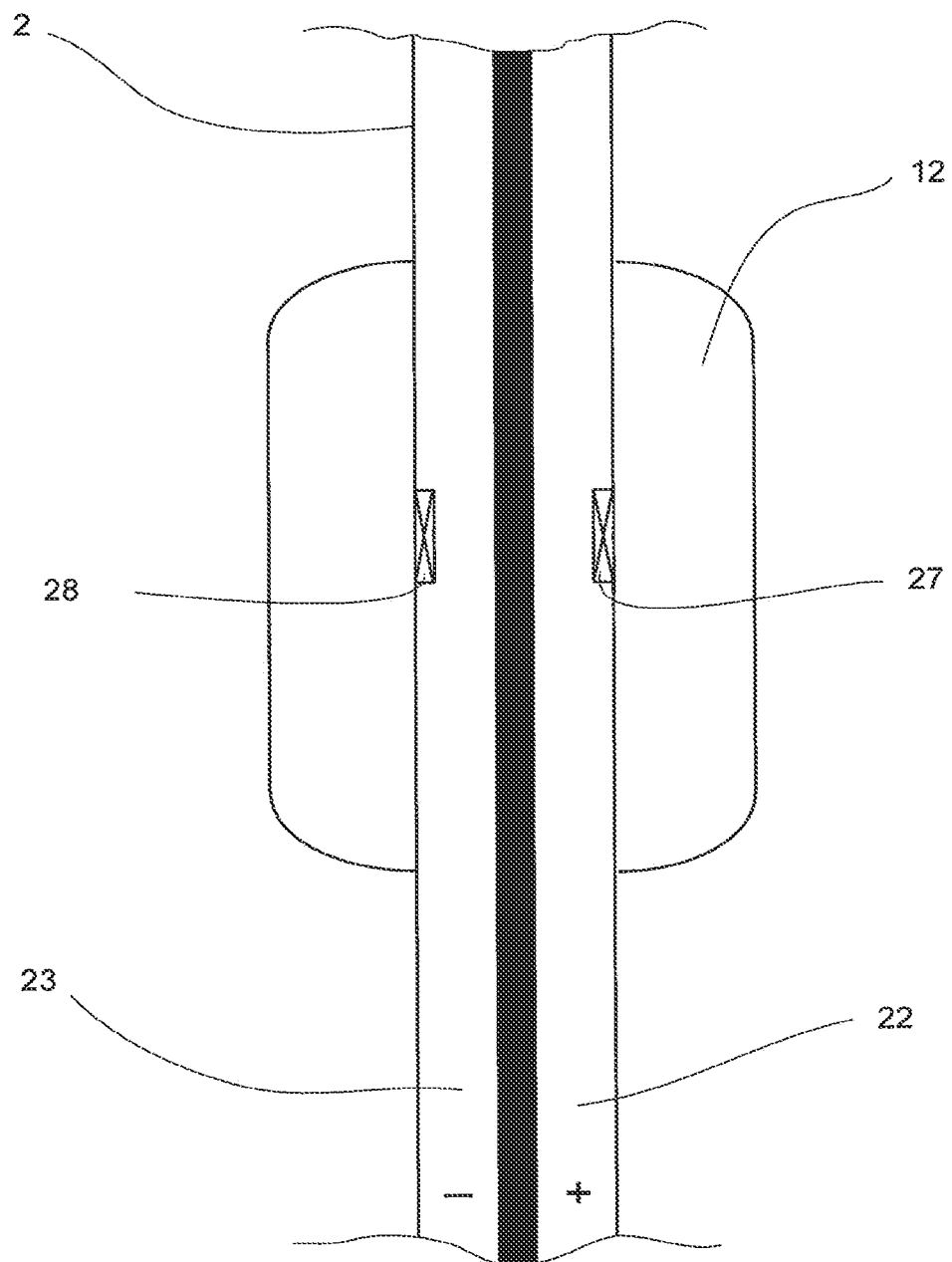
FIG. 3 shows an enlarged illustration of the part of the catheter bearing the balloon, in section.

In FIG. 3, the partial region of the balloon 12, which is connected in a sealing manner to the catheter 2, is illustrated on an enlarged scale. The two lumina leading away from the fluid pump 7 and back to the fluid pump 7 are designated in turn by 22 and 23. In the region of the balloon 12, the wall of these lumina is provided with valves which can be actuated magnetically for example. The valves are indicated diagrammatically by 27 and 28. An opening of the valve 27 leads to the fluid, coming from the fluid pump 7, which is under pressure, which is indicated by the "+" sign, being pumped into the balloon 12, with which the overall quantity of the circulating driving fluid would of course be reduced, in so far as the reservoir 11, indicated diagrammatically in FIG. 1, is not provided. By closing the valve 27, the occlusion is closed off, the collapsing of the balloon 12 being able to be brought about by opening the valve 28 and the fluid now being drawn off via the lumen 23, leading back to the pump, which lumen 23 is at a slightly lower pressure which is indicated by the "−" sign. As the overall volume of the fluid in the circulating system is now to be reduced, a portion of this volume must be pumped back again into the reservoir 11 according to FIG. 1.

The invention claimed is:
1. A system for assisting the blood circulation of a heart, comprising:
a heart assist pump device deliverable to the heart and comprising:
an inflow tube defining a blood inflow path and having a suction end insertable into a ventricle of the heart;
a magnetically driven rotor assembly configured to be axially aligned with the inflow tube and to be spaced apart from the suction end when the suction end of the inflow tube is inserted into the ventricle, the magnetically driven rotor assembly comprising a first magnetic device that is rigidly coupled to and axially adjacent to a rotor having guide surfaces to produce centrifugal flow components, the magnetically driven rotor assembly being rotatable about a central axis within a surrounding stationary housing to act upon blood flowing from the inflow tube to the rotor while the magnetically driven rotor assembly is entirely spaced apart from the stationary housing by a gap sized for passage of the blood;
a second magnetic device axially aligned with the inflow tube and positioned to magnetically drive rotation of the magnetically driven rotor assembly via a magneto coupling with the first magnetic device while being spaced apart and sealed from both the rotor and the first magnetic device of the magnetically driven rotor assembly, the second magnetic device being positioned axially spaced apart from the guide surfaces of the rotor;
a blood outflow port positioned radially adjacent the guide surfaces of the rotor such that, when the blood is driven by the magnetically driven rotor assembly, the blood exits the surrounding stationary housing in a direction substantially perpendicular to the central axis of the magnetically driven rotor assembly, wherein the magneto coupling is configured to both drive rotation of the magnetically driven rotor assembly and orient the magnetically driven rotor assembly such that the magnetically driven rotor assembly remains entirely spaced apart from the surrounding stationary housing by the gap sized for passage of the blood; and an external control unit configured to regulate operation of the second magnetic device based upon a control value indicative of cardiac output, wherein the external control unit is connectable to the heart assist pump device for controlling the second magnetic device to thereby magnetically drive the rotation of the magnetically driven rotor assembly via the magneto coupling with the first magnetic device.

2. The system of claim 1, wherein the first magnetic device is configured to be positioned between the second magnetic device and the guide surfaces of the rotor of the magnetically driven rotor assembly.

3. The system of claim 2, wherein the first magnetic device is configured to rotate together with the rotor relative to the surrounding stationary housing.

4. The system of claim 3, wherein the second magnetic device is positioned closer to the blood outflow port than to the suction end of the inflow tube.

5. The system of claim 1, wherein the magnetically driven rotor assembly is sealed from the second magnetic device and a drive source configured to regulate the operation of the second magnetic device.

6. The system of claim 5, wherein the drive source comprises a hydraulically or pneumatically operated drive wheel.

7. The system of claim 1, further comprising one or more sensors configured to deliver feedback signals to the external control unit.

8. The system of claim 7, wherein the external control unit is connectable to the heart assist pump device to deliver energy to the second magnetic device.

9. The system of claim 8, wherein the external control unit is configured to deliver energy to the second magnetic device via delivery of a driving fluid.

10. The system of claim 1, wherein the heart assist pump device is a catheter device.

11. The system of claim 1, wherein the first magnetic device comprises a bar magnet.

12. The system of claim 1, wherein the second magnetic device comprises a bar magnet.

13. The system of claim 1, wherein the second magnetic device is configured to rotate during rotation of the magnetically driven rotor assembly.

14. The system of claim 13, further comprising a drive wheel configured to urge rotation of the second magnetic device.

15. The system of claim 1, wherein the heart assist pump device is formed as an intravasal rotary pump.

16. A system for assisting blood circulation of a heart, the system comprising:

a heart assist pump device deliverable to the heart and comprising:

an inflow tube defining a blood inflow path along an inflow axis and being insertable into a left ventricle;

chamber walls at least partially defining a chamber to receive blood from the inflow tube;

a magnetically driven rotor assembly configured to be axially aligned with the inflow axis and comprising a first magnetic device that is rigidly coupled to and axially adjacent to a rotor having guide surfaces to produce centrifugal flow components, the rotor and the first magnetic device of the magnetically driven rotor assembly being rotatable within the chamber about an axis of rotation aligned with the inflow axis to drive the blood flowing from the inflow tube;

a magnetic drive system comprising a second magnetic device axially aligned with the inflow axis and spaced apart from the magnetically driven rotor assembly such that a wall of the chamber walls defining the chamber is positioned between the magnetically driven rotor assembly and the second magnetic device, the second magnetic device positioned axially closer to the first magnetic device than to the rotor of the magnetically driven rotor assembly so as to magnetically drive rotation of the magnetically driven rotor assembly within the chamber via a magneto coupling with the first magnetic device; and a blood outflow port positioned radially outward of the guide surfaces of the rotor such that, when the blood is driven by the magnetically driven rotor assembly, the blood exits the chamber in a direction substantially perpendicular to the inflow axis, wherein the magneto coupling is configured to both drive rotation of the magnetically driven rotor assembly and orient the magnetically driven rotor assembly such that the magnetically driven rotor assembly remains entirely spaced apart from the chamber walls by a gap sized for passage of the blood; and an external control unit configured to control operation of the second magnetic device based on a control value indicative of cardiac output, wherein the external control unit is connectable to the heart assist pump device for controlling the second magnetic device to thereby magnetically drive the rotation of the magnetically driven rotor assembly via the magneto coupling with the first magnetic device.

17. The system of claim 16, wherein the first magnetic device is rigidly coupled to the rotor of the magnetically driven rotor assembly at a position between the second magnetic device and the rotor.

18. The system of claim 16, wherein said gap sized for passage of the blood is configured to be occupied by the blood when the second magnetic device drives the rotation of the magnetically driven rotor assembly.

19. The system of claim 18, wherein the gap surrounds the magnetically driven rotor assembly.

20. The system of claim 18, wherein at least part of the gap extends radially outward from the magnetically driven rotor assembly.

21. The system of claim 20, wherein at least part of the gap extends along a face of the magnetically driven rotor assembly that is axially opposite from the inflow tube.

22. The system of claim 16, wherein the chamber is a first chamber within which the magnetically driven rotor assembly is positioned, and the magnetic drive system is positioned within a second chamber sealed from the first chamber.

23. The system of claim 22, wherein said wall of the chamber walls separates the first chamber from the second chamber.

24. The system of claim 16, wherein the first magnetic device comprises a permanent magnet.

25. The system of claim 16, wherein the second magnetic device comprises a permanent magnet.

26. The system of claim 16, further comprising one or more sensors configured to deliver feedback signals to the external control unit.

27. The system of claim 16, wherein the external control unit is configured to deliver energy to the second magnetic device via delivery of a driving fluid.

28. The system of claim 16, wherein the heart assist pump device is a catheter device.

29. The system of claim 16, wherein the magnetically driven rotor is positioned within a catheter.

30. The system of claim 16, wherein the heart assist pump device further comprises a drive wheel configured to urge rotation of the second magnetic device.

* * * * *